United States Patent [19]

Nelson et al.

[11] Patent Number: 4,680,300

[45] Date of Patent: Jul. 14, 1987

[54] ANTI-INFLAMMATORY GUANIDINES

[75] Inventors: Peter Nelson, Los Altos; Stefan H. Unger, Palo Alto, both of Calif.

[73] Assignee: Syntex (U.S.A.) Inc., Palo Alto, Calif.

[21] Appl. No.: 690,295

[22] Filed: Jan. 10, 1985

[51] Int. Cl.[4] .................. A61K 31/47; A61K 31/155; C07C 129/00

[52] U.S. Cl. .................. 514/312; 564/237; 546/153; 546/157; 546/163; 548/193; 548/198; 548/214; 514/313; 514/370; 514/372; 514/634; 514/852

[58] Field of Search ............... 564/237; 514/312, 313, 514/634, 370, 372, 882, 852; 546/153, 157, 163; 548/193, 198, 214

[56] References Cited

U.S. PATENT DOCUMENTS

| | | | |
|---|---|---|---|
| 3,159,676 | 12/1964 | Spickett et al. | 564/237 |
| 3,159,679 | 12/1964 | Spickett | 260/564 |
| 3,184,473 | 5/1965 | Durant | 260/309.6 |
| 3,200,151 | 8/1965 | Spickett | 260/564 |
| 3,201,459 | 8/1965 | Coda | 260/501 |
| 3,209,023 | 2/1965 | Copp | 260/501 |
| 3,211,789 | 10/1965 | Hselte | 260/564 |
| 3,246,031 | 4/1966 | Campbell | 260/501 |
| 3,456,058 | 7/1969 | Schumann | 514/634 |
| 3,474,134 | 10/1969 | Copp | 260/501.14 |
| 3,574,744 | 4/1971 | Krapcho | 260/558 |
| 4,152,435 | 5/1979 | Durant | 424/273 |

FOREIGN PATENT DOCUMENTS

| | | |
|---|---|---|
| 831100 | 2/1952 | Fed. Rep. of Germany . |
| 1934014 | 3/1970 | Fed. Rep. of Germany . |
| 1031165 | 7/1961 | United Kingdom . |
| 1007844 | 8/1963 | United Kingdom . |
| 1026402 | 4/1966 | United Kingdom . |
| 1256764 | 12/1971 | United Kingdom . |
| 129443 | 10/1972 | United Kingdom . |
| 2076397 | 4/1981 | United Kingdom . |
| 1604674 | 12/1981 | United Kingdom . |

OTHER PUBLICATIONS

Durant, G. J. et al., *J. Med. Chem.*, vol. 9, (1966), pp. 22–27.

Primary Examiner—Paul J. Killos
Assistant Examiner—L. Hendriksen
Attorney, Agent, or Firm—David A. Lowin; Tom M. Moran

[57] ABSTRACT

A compound having the formula

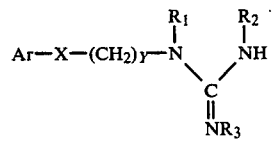

where
 Ar=naphthyl, biphenyl, or quinolinyl;
 X=oxygen or NH;
 Y=2 to 8;
 $R_1$=phenyl, substituted phenyl, hydrogen, lower alkyl; and
 $R_2$ is the same or different from $R_3$ and is alkyl, cycloalkyl, phenyl, substituted phenyl, thiazolyl; and
 the pharmaceutically acceptable salts thereof.

Compounds of this general formula are useful as anti-inflammatories, and as anti-psoriatic agents.

21 Claims, No Drawings

ANTI-INFLAMMATORY GUANIDINES

BACKGROUND OF THE INVENTION

This invention relates to a series of guanidine derivatives characterized by an (aryloxy or arylamino) alkyl substituent. In particular, this invention relates to guanidine derivatives useful as anti-inflammatory agents.

Substituted guanidines are known in the art. U.S. Pat. No. 3,159,676 issued to Spickett et al discloses a series of arylamino and aryloxy alkyl guanidines. These guanidines have only one of the three guanidine nitrogens substituted with other than hydrogen atoms. Other similar examples include *J Med Chem* 9, 22 (1966) in which a variety of substituted phenoxy alkyl guanidines were reported to have anti-inflammatory properties. The substituents on the benzene ring in that reference are lower alkyl or halogen.

SUMMARY OF THE INVENTION

This invention provides compounds having the formula

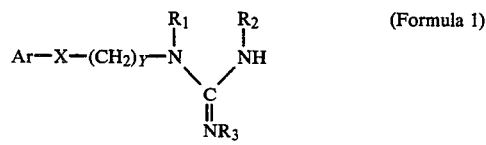

(Formula 1)

where
Ar=naphthyl, biphenyl, or quinolinyl;
X=oxygen or NH;
Y=2 to 8;
$R^1$=phenyl, substituted phenyl, hydrogen, lower alkyl; and
$R_2$ is the same or different from $R_3$ and is alkyl, cycloalkyl, phenyl, substituted phenyl, thiazolyl; and the pharmaceutically acceptable salts thereof.

Preferred compounds are those wherein Ar is naphthyl, especially 1-naphthyl, Y is 6 to 8, and X is O $R_1$ is hydrogen, and $R_2$ is the same as $R_3$ and $R_2$ and $R_3$ are selected from the group consisting of phenyl and optionally substituted phenyl. Particularly preferred compounds include those where $R_2$ and $R_3$ are lower alkyl phenyl and lower alkoxy phenyl, particularly preferred when $R_2$ and $R_3$ are 2-methylphenyl.

DETAILED DESCRIPTION OF THE INVENTION

Definitions

As used herein:

"Alkyl" means a branched or unbranched saturated hydrocarbon chain containing 1-8 carbon atoms, such as methyl, ethyl, propyl, tert-butyl, n-hexyl, n-heptyl or iso-octyl and the like.

"Alkoxy" means the group —OR wherein R is alkyl as herein defined.

"Cycloalkyl" means saturated carbocyclic rings containing 5-7 carbon atoms.

"Alkylene" means $(CH_2)_n$ wherein n is an integer from 2-8.

"Optional" or "optionally" means that the subsequently described event or circumstance may or may not occur, and that the description includes instances where said event or circumstances occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not. "Optionally substituted phenyl" means a phenyl moiety, which may or may not be substituted as indicated in the previous paragraph, with 1-3 substituents selected from the group consisting of halo, lower alkyl, lower alkoxy, where lower refers to fewer than four carbon atoms, and hydroxy. "Substituted phenyl" means a phenyl moiety that is so-substituted.

The guanidines of this invention contain basic nitrogens that can be reacted with mineral or organic acids to form pharmaceutically acceptable acid addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

METHODS OF PREPARATION

Substituted guanidines can be synthesized by several methods well known to the art. For example, "Methoden Der Organishe Chemie (Houben-Weyl)" Vol. VIII, p. 180-188 describes methods for preparing guanidines.

In equations 1 through 7, $R^4$, $R^5$, and $R^6$ can be any substituent to give a guanidine of Formula 1, although it should be realized that the reactions that are represented are general for all guanidines.

Guanidines can be synthesized by reacting a primary amine with a cyanoamine. The particular guanidine produced depends on the substituents present on the amine and cyanoamine starting materials (Equation 1). Approximately equimolar amounts of the starting materials are heated together at from about 50° C. to about 250° C., preferably, at about 170° C. A polar organic solvent such as ethanol or dimethylformamide (DMF) may be optionally used.

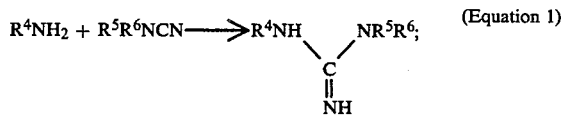

(Equation 1)

The cyanoamine starting materials can be conveniently synthesized by heating a mixture of an appropriately substituted amine and an equimolar amount of cyanogen bromide in the presence of an inert organic solvent such as benzene (Equation 2)

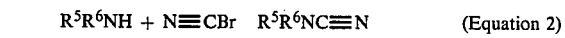

(Equation 2)

The reactants are heated at from about 50° to reflux temperature, for from 1 to 24 hours.

Guanidines can be synthesized by reacting together an amine and either an appropriately substituted urea or, more preferably, an appropriately substituted thiourea (Equation 3). A mixture of equimolar amounts of each of the reactions, dissolved in a polar organic solvent such as methanol or ethanol, is heated. The reaction proceeds at a temperature in the range of about 50° to reflux temperature, preferably at reflux temperature. The reaction is continued from 6 to 48 hours. *Synthetic Organic Chemistry* by R. B. Wagner and H. B. Zook. p. 645–652 and 827–831 describes methods to synthesize the urea and thiourea starting materials.

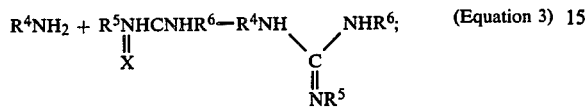
(Equation 3)

where X=O or S.

Guanidines can be synthesized by reacting a primary amine and either an appropriately substituted alkyl isourea or an appropriately substituted alkyl isothiourea (Equation 4). Equimolar amounts of the reactants are heated together at a temperature of from about 50° C. to about 150° C., preferably about 100° C. The reaction may optionally be conducted in a polar solvent such as methanol, ethanol or DMF.

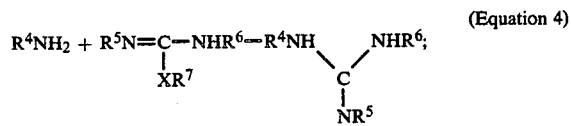
(Equation 4)

where X=O or S, $R^7$=alkyl.

The alkyl isourea and alkyl isothiourea starting materials can be prepared by any standard methods. For example, they may be prepared by the alkylation reaction of, for example, methyl iodide, and a thiourea, or by the reaction between a chloroimine compound $R_2N=C(Cl)—NHR_3$ and an alcohol or mercaptan (Equation 5).

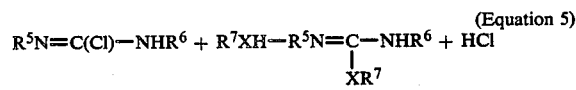
(Equation 5)

X=O or S, $R_7$=alkyl.

Guanidines can be synthesized by reacting an amine and a substituted carbodiimide (Equation 6). Equimolar amounts of the reactants are heated together at a temperature of between 50° C. and 150° C., preferably about 100° C., for about ½ to 12 hours. The reaction proceeds well in an optional inert organic solvent such as tetrahydrofuran or DMF.

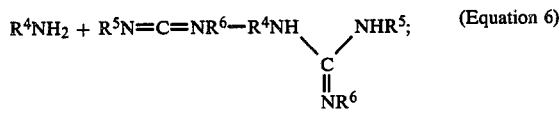
(Equation 6)

The carbodiimide starting material is conveniently synthesized by, for example, the treatment of a urea with a dehydrating agent such as toluenesulfonyl chloride and pyridine (Equation 7)

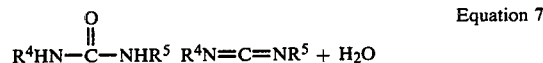
Equation 7 or by the oxidation of a thiourea using, for example, mercuric oxide.

The compounds of Formula 1 in free base form may be converted to the acid addition salts by treating with a stoichiometric excess of the appropriate organic or inorganic acid, for example, hydrochloric acid, nitric acid, sulfuric acid, malic acid, and the like. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula 1 may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula 1 may be interchanged by taking advantage of differential solubilities of the salts, volatilities or acidities of the acids, or by treating with the appropriately loaded ion exchange resin. For example, the interchange is effected by the reaction of a salt of the compounds of Formula 1 with a slight stoichiometric excess of an acid of a lower pK than the acid component of the starting salt. This conversion is carried out at a temperature between about 0° C. and the boiling point of the solvent being used as the medium for the procedure.

The compounds of Formula 1 have been shown in standard laboratory tests to inhibit inflammation. Thus, the antiinflammatory activity of compounds of Formula 1 can be demonstrated by standard in vitro laboratory tests, such as by their ability to inhibit the enzymes phospholipase and lipoxygenase, or to inhibit the chemotaxis of leukocytes, or to inhibit the generation of superoxide. The antiinflammatory activity of compounds of Formula 1 can also be demonstrated by standard in vivo laboratory tests, such as by their ability to inhibit carageenan-induced pleural inflammation in rats, or to inhibit adjuvant arthritis in rats, or to inhibit topical inflammation induced by croton oil, oxazolone or arachidonic acid in rats or mice. Accordingly, the compounds of Formula 1 or their salts or pharmaceutical compositions containing them, may be used in inhibiting, preventing, or controlling inflammation in mammals. In addition, the compounds of Formula 1 have been shown to be effective as anti-psoriatic agents.

The antipsoriatic activity of compounds of Formula I can be demonstrated by the ability of the compounds to inhibit psoriasis in humans. One skilled in the art will recognize that other tests may be applicable for verifying anti-inflammatory or anti-psoriatic activity.

Administration of the active compounds and salts described herein can be via any of the accepted modes of administration for agents that control inflammation. These methods include oral, parenteral and otherwise systemic or topical.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single adminstration of precise dosages. The compositions will include a conventional pharmaceutical carrier or excipient and an active compound of Formula 1 or the pharmaceutically acceptable salts thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of formula 1, either oral or topical administration is preferred depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

For topical administration, these compositions comprise an effective amount of a compound of this class in admixture with a pharmaceutically acceptable non-toxic carrier. A suitable range of composition would be 0.1%–10% active ingredient, and the balance carrier, preferably 1–2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the instant invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and palmitic acid; and 0 to 20 wt. percent of a penetrant such as dimethyl sulfoxide, or dimethylacetamide.

The amount of active compound administered will of course, be dependent on the subject being treated, the severity of the affliction, the manner of administration and the judgment of the prescribing physician. However, an effective dosage is in the range of 1–100 mg/kg/day, preferably about 25 mg/kg/day. For an average 70 kg human, this would amount to 70 mg–7 g per day, or preferably about 1.5 g/day.

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The compounds of Formula 1 may be formulated with suitable pharmaceutical vehicles known in the art to form particularly effective topical compositions. An effective amount of the guanidine compound is about 0.001% w/w to about 10% w/w of the total formulated composition. The rest of the formulated composition will be about 90% w/w to about 99.999% w/w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any standard drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the quanidine compounds therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture | 50–99 parts by weight |

| | |
|---|---|
| (15% or more glycol) | |
| Fatty Alcohol | 1-20 |
| Non-ionic Surfactant | 0-10 |
| Mineral Oil | 0-10 |
| Typical pharmaceutical Adjuvants | 0-5 |
| Active Ingredients | 0.001-10 |

The fatty alcohol, non-ionic surfactant, and other adjuvants are discussed in U.S. Pat. No. 3,934,013 to Poulsen which is incorporated herein by reference.

The compounds of Formula 1 may also be formulated as topical ointments. The standard ointment is a semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical standard ointment base:

| | |
|---|---|
| White Petrolatum | 40-94 parts by weight |
| Mineral Oil | 5-20 |
| Glycol Solvent | 1-15 |
| Surfactant | 0-10 |
| Stabilizer | 0-10 |
| Active Ingredients | 0.001-10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001-10.0 parts by weight |
| Propylene Carbonate | 1-10 |
| Solvent | 1-10 |
| Surfactant | 0-10 |
| White Petrolatum | 70-97 |

Suitable solvents, surfactants, stabilizers, etc. are discussed in U.S. Pat. No. 3,934,013 and such as incorporated herein by reference.

A suitable topical anhydrous, water washable, ointment type, base is described in U.S. Pat. No. 3,592,930 to Katz and Neiman, and that patent is incorporated herein by reference. A representative composition of this invention utilizing such base is as follows:

| | |
|---|---|
| Glycol Solvent | 40-35 parts by weight |
| Fatty Alcohol | 15-45 |
| Compatible Plasticizer | 0-15 |
| Compatible Coupling Agent | 0-15 |
| Penetrant | 0-20 |
| Active Ingredients | 0.001-10.0 |

Another aspect of the invention is a method for relieving the condition of psoriasis in a mammal by topically administering a composition containing a compound of Formula 1. Generally, the anti-psoriatic manifestation in mammals, particularly humans, is combatted by contacting the inflamed areas with a therapeutically effective amount of the guanindine-containing compositions of this invention, that is, an amount which results in a lessening of the epidermal cell proliferation (an anti-psoriatic effect). Preferably the guanidines are first formulated to prepare a suitable pharmaceutical formulation, as discussed hereinabove, which is then placed in contact with the afflicted area(s). An effective amount of the guanidine compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to effect an anti-psoriatic response, but not enough to adversely effect the recipient, is applied to the afflicted area(s).

EXAMPLES

Preparation 1

1-Amino-6-(7-chloro-4-quinolinyl)hexane 17.1 Grams of hexane-1,6-diamine and 4.3 g of 4,7-dichloroquinoline were mixed together and heated to 150° C. for four hours. The reaction was cooled and water and methylene chloride were then added. The organic phase was washed, dried with anhydrous magnesium sulfate and evaporated thereby affording 1-amino-6-(7-chloro-4-quinolinyl)hexane having a melting point of 133°-134°.

Other compounds that can be made by the same general synthetic method by appropriate substitution of starting materials include:
1-amino-6(4-quinolinyl)hexane
1-amino-2(4-quinolinyl)ethane
1-amino-4(4-quinolinyl)butane
1-amino-8(4-quinolinyl)octane

Preparation 2

1-AMINO-8-(1-NAPHTHYLOXY)OCTANE

2(A) Preparation of 1-chloro-8-(p-toluenesulphonyloxy)octane 20.5 Grams of p-toluenesulphonyl chloride were added to a mixture of 17.7 g 8-chloro-1-octanol and 50 ml of pyridine at 0°. After an hour the solution was added to ice and the mixture was extracted with ether. The ethereal solution was washed with dilute hydrochloric acid, dried with magnesium sulfate, and evaporated to yield the title compound as an oil.

In a similar manner, using the appropriate ω-chloroalkanols, the following compounds were prepared:
1-chloro-2-(p-toluenesulphonyloxy)ethane
1-chloro-3-(p-toluenesulphonyloxy)propane
1-chloro-4-(p-toluenesulphonyloxy)butane
1-chloro-5-(p-toluenesulphonyloxy)pentane
1-chloro-6-(p-toluenesulphonyloxy)hexane
1-chloro-7-(p-toluenesulphonyloxy)heptane 2(B) 1-Chloro-8-(1-naphthyloxy)octane A mixture of 1-naphthol (12.9 g), potassium carbonate (23.5 g), 1-chloro-8-(p-toluenesulphonyloxy)octane (23.5 g) and dimethylformamide (200 ml) was stirred at 55° for 2-½ days. The solution was then cooled and added to water, and extracted with ether. The extract was dried and evaporated and the residue was chromatographed on silica gel (750 g), eluting with 3:1 hexane: methylene chloride, so as to afford the title compound as an oil.

Similarly, using the procedure in paragraph A and B but substituting a different 1-chloro-ω-(p-toluenesulphonyloxy)alkane, the corresponding 1-chloro-ω-(1-naphthyloxy) alkanes are obtained.

2(C) 1-Amino-8-(1-naphthyloxy)octane 9.5 g of 1-chloro-8-(1-naphthyloxy)octane and 8.4 g of potassium phthalimide were taken up in 50 ml DMF and the resulting solution was heated at 140° for 3 hours. The reaction solution was then poured into water and extracted with dichloromethane. The extract was washed, dried and evaporated and the residue was crystallized from acetone/hexane to afford the intermediate N-[8-(1-naphthyloxy)octyl]phthalimide mp 63°–64°.

A solution of 10.0 g N-[8-(1-naphthyloxy)octyl]phthalimide, prepared as above, and 200 ml of ethanol and 3.2 ml of hydrazine hydrate was refluxed for 18 hours. The solution was evaporated to about 100 ml, and diluted with 200 ml of water, then basified with aqueous potassium hydroxide and extracted with hexane. The extract was washed, dried and evaporated to give the title compound as an oil which was converted to the hydrochloride, mp 90.5°–92°.

Similarly, using the procedures of (B) and (C) above, but employing the appropriate 1-chloro-ω-(p-toluenesulphonyloxy)alkanes instead of 1-chloro-8-(p-toluenesulphonyloxy)octane, the following compounds were prepared:

1-amino-4-(1-naphthyloxy)butane mp 99°–102° (maleate);
1-amino-5-(1-naphthyloxy)pentane mp 169°–172° (hemimaleate);
1-amino-6-(1-naphthyloxy)hexane mp 112°–114° (hemimaleate).

Similarly, using the procedures of (B) and (C) above, but employing 1-chloro-2-(p-toluenesulphonyloxy)ethane instead of 1-chloro-8-(p-toluenesulphonyloxy)octane, the following compound is prepared 1-amino-2-(1-naphthyloxy)ethane.

Preparation 3

1-AMINO-8-(2-NAPHTHYLYLOXY)OCTANE

3(A) Preparation of 1-(2-Naphthyloxy)-8-chlorooctane

A mixture of 17.5 g 2-naphthol, 32.0 g of 1-chloro-8-(p-toluenesulphonyloxy)octane, 32.0 g of anhydrous potassium carbonate and 200 ml of DMF was stirred at 60° for 4 hours. Water and ether were then added, the ethereal solution was separated, and washed with water and dilute aqueous potassium hydroxide, then dried and evaporated. The residue was chromatographed on silica gel, eluting with 3:2 hexane: dichloromethane, to afford the title compound as a solid, mp 35°.

3(B) 1-Amino-8-(2-naphthyloxy)octane

1-Chloro-8-(2-naphthyloxy)octane (4.75 g) and potassium phthalimide (4.2 g) were heated in dimethylformamide (25 ml) at 120° for 4 hours. The solution was then cooled, added to water, and extracted with methylene chloride. The extracts were then dried and evaporated to afford N-[8-(2-naphthyloxy)octyl]phthalimide as a gum. This material was refluxed for 16 hours in ethanol (150 ml) containing 85% aqueous hydrazine hydrate (3 ml). The solution was cooled and water (450 ml) and 10% aqueous potassium hydroxide (50 ml) were added. The resultant solution was extracted with hexane; the extract was dried and evaporated to afford the title compound as an oil (hydrochloride mp 169°–170°).

Similarly, using the procedure of (a) and (b) above, but employing the appropriate 1-chloro-ω-(p-toluenesulphonyloxy)alkane instead of 1-chloro-8-(p-toluenesulphonyloxy)octane, the following compounds are prepared:

1-amino-2-(2-naphthyloxy)ethane;
1-amino-4-(2-naphthyloxy)butane;
1-amino-7-(2-naphthyloxy)heptane.

Preparation 4

1-AMINO-6-(2-BIPHENYLOXY)HEXANE

4(A) 1-(2-Biphenyloxy)-6-chlorohexane

1-Chloro-6-(p-toluenesulphonyloxy)hexane (100 g), 2-hydroxybiphenyl (59 g) and potassium carbonate (60 g) were heated with stirring in dimethylformamide at 70° for 16 hours. The solution was cooled and added to water, then extracted with ether. The extract was washed with water, dried and evaporated, and the residue was chromatographed on silica gel (1800 g) eluting with 99:1 hexane; ethyl acetate, so as to afford the title compound as an oil.

4(B) N-[6-(2-biphenyloxy)hexyl]phthalimide

A solution of 1-(2-biphenyloxy)-6-chlorohexane 8.0 g) and potassium phtalimide (5.6 g) in dimethylformamide (100 ml) was heated at reflux temperature for 3 hours. The solution was cooled and poured into water, and the product was extracted out with ethyl acetate. The extract was dried and evaporated to afford N-[6-(biphenyloxy)hexyl]phthalimide.

Similarly, using the procedures of A and B above, but employing the appropriate chloro p-toluenesulphonyloxyalkane instead of 1-chloro-6-toluenesulphonyloxyhexane, the following compounds were prepared:

N-[4-(2-biphenyloxy)-butyl]phthalimide; and
N-[8-(2-biphenyloxy)-octyl]phthalmide.

4(C) 1-Amino-6-(biphenyloxy)hexane

A mixture of N-[6-(2-biphenyloxy)hexyl]phthalimide (15.1 g), ethanol (400 ml) and hydrazine hydrate (30 ml) was heated at reflux for 4 hours, cooled to room temperature, filtered, and evaporated to dryness. The material that remained was stirred with dichloromethane (500 ml), filtered and evaporated to yield 1-amino-6-(2-biphenyloxy) as an oil, which was converted to the hydrochloride salt, (m.p. 86°–88° CC.) according to the method of Example IV.

Following the procedure described above in paragraph 4(B) of this Preparation, but substituting the appropriate N-(2-biphenyloxy)alkyl]phthalimide, the following compounds were prepared and converted to pharmaceutically acceptable salts:

1-amino-4-(2-biphenyloxy)-butane, as the hydrochloride, mp 162°–164° C.; and
1-amino-8-(2-biphenyloxy)-octane, as the hydrochloride, mp 136° C.

Similarly, using the procedures 4(A), 4(B) and 4(C) above, but employing 3-hydroxybiphenyl or 4-hydroxybiphenyl in place of 2-hydroxybiphenyl, and the appropriate 1-chloro-ω-(p-toluenesulphonyloxy)alkane, the following compounds were prepared:

1-amino-6-(3-biphenyloxy)hexane(hydrochloride), mp 120°-122°;

1-amino-4-(4-biphenyloxy)butane(hydrochloride), mp 202°-205°;

1-amino-5-(4-biphenyloxy)pentane(hydrochloride), mp 244°-246°;

1-amino-6-(4-biphenyloxy)hexane(hydrochloride), mp 201°-202°;

1-amino-7-(4-biphenyloxy)heptane(hydrochloride), mp 228°-230°; and 1-amino-8-(4-biphenyloxy)octane(hydrochloride), mp 179°-182°.

Preparation 5

Diphenylcarbodiimide 1,3-Diphenylthiourea (22.8 g), triphenylphosphine (10.1 g) triethylamine (10.1 g) and carbon tetrachloride (21.6 g) were refluxed for 4 hours in methylene chloride (300 ml). The solvent was removed under vacuum. The residue was shaken with hexane (300 ml); the hexane solution was evaporated and the residue was distilled to afford the title compound as an oil bp 115°-120°/0.3 mm. Similarly, by using this procedure, but employing other 1,3-disubstituted thioureas instead of 1,3-diphenylthiourea, other carbodiimides can be made.

Preparation 6

1,3-di(2-methylphenyl)-S-methylisothiourea 1,3-di(2-methylphenyl)thiourea (60.0 g) and methyl iodide (36.5 g) were refluxed for 3 hours in ethanol (1200 ml). The solution was cooled and about 600 ml ethanol was removed under vacuum. First water (50 ml), and then saturated aqueous sodium bicarbonate were added to the ethanol solution until the pH was 7-8. Water (1000 ml) was then added to the solution and the solid was filtered off and washed with water before being dried under vacuum to afford the title compound.

Similarly, by using this procedure, but employing other 1,3-disubstituted thioureas instead of 1,3-di(2-methylphenyl)thioures other 1,3-disubstituted S-methylisothioureas can be prepared.

For example, using the method of Preparation 6 the following are prepared
- 1,3-di(3-methylphenyl)-S-methylisothiourea;
- 1,3-di(4-methylphenyl)-S-methylisothiourea
- 1,3-diphenyl-S-methylisothiourea; and
- 1,3-di(2-ethylphenyl)-S-methylisothiourea

EXAMPLE I 1,2-Dicyclohexyl-3-[8-(1-naphthyloxy)octyl]guanidine

700 Milligrams (mg) of 1-amino-8-(1-naphthyloxy)octane and 505 mg of dicyclohexylcarbodiimide were mixed well and heated to 120° C. for 1 hour. The crude product was chromatographically separated on a silica gel column eluting with a mobile phase of 25 parts 2-propanol to 1 part water to 1 part acetic acid affording 1,2-dicyclohexyl-3-[8-(1-naphthyloxy)octyl]guanidine as a gum.

EXAMPLE II 1,2-diphenyl-3(8-(2-naphthyloxy)octyl)guanidine 4.0 g of 1-amino-8(2-naphthyloxy)octane and 3.6 g of 1,3-diphenyl-S-methylisothiourea were heated to 110° C. under a nitrogen atmosphere for 3 hours. The crude product was chromatographically separated from the reaction mixture on a silica gel column with the mobile phase being methylene chloride:methanol:ammonium hydroxide 100:12:1.2 thereby isolating the 1,2-diphenyl-3-[8-(2-naphthyloxy)octyl]guanidine which was converted to the hydrochloride (mp 124°-126°) using the procedure of Example IV.

In a similar manner, using the appropriate amines and isothioureas, the following compounds were prepared
1,2-Diphenyl 3-[6-(7-chloro-quinolinyl)-hexyl]guanidine trihydrochloride, mp 99°;

1,2-dicyclohexyl-3[6-(7-chloro-4-quinolinyl))hexyl]guanidine, mp 122°-124°;

1,2,3-triphenyl-3-[8-(1-naphthyloxy)octyl]guanidine maleate, mp 43°-45°;

1,2-di-(2-methylphenyl)-3-[8-(1-naphthyloxy)octyl]guanidine hydrochloride, mp 124°-126°;

1,2-di-(2-methoxyphenyl)-3[8-(1-naphthyloxy)octyl]guanidine, mp 90°-92°;

1,2-diphenyl-3-[2-(2-naphthyloxy)ethyl]guanidine mp, 138°-9°;

1,2-dicyclohexyl-3-[2-(2-naphthyloxy)ethyl]guanidine diphosphate, mp 96°-98°;

1,2-di-4-(ethoxyphenyl)-3-[2-(2-naphthyloxy)etyl]guanidine dihydrochloride, mp 177°-180°;

1-cyclohexyl-2-(2-thiazolyl)-3-[2-(2-naphthyloxy)ethyl]guanidine, mp 129°-131°;

1,2-di-(4-methylphenyl)-3-[2-(2-naphthyloxy)ethyl]guanidine, mp 118°-120°;

1,2-diphenyl-3-ethyl-3-[2-(2-naphthyloxy)ethyl]guanidine, mp 109°-110°;

1,2-diphenyl-3-[2-(4-phenylphenoxy)ethyl]guanidine hydrochloride, mp 185°-188°; and 1,2-diphenyl-3-[2-(4-phenylphenoxy)ethyl]guanidine, mp 100°-102°.

Similarly, using the procedure of Example II above, but employing the appropriate amines and isothioureas, the following are obtained:
- 1,2-di-(3-methylphenyl)-3-[8-(1-naphthyloxy)octyl]guanidine;
- 1,2-di-(4-methylphenyl)-3-[8-(1-naphthyloxy)octyl]guanidine;
- 1,2-di-(2-ethylphenyl)-3-[8-(1-naphthyloxy)octyl]guanidine;
- 1,2-di-(2-methylphenyl)-3-[7-(1-naphthyloxy)heptyl]guanidine;
- 1,2-di-(2-methylphenyl)-3-[6-(1-naphthyloxy)hexyl guanidine; and
- 1,2-di-(2-methylphenyl)-3-[8-(2-naphthyloxy)octyl]guanidine.

EXAMPLE III 1,3-Diphenyl-1-[8-(1-naphthyloxy)octyl]guanidine

A The preparation of
1-(1-Naphthyloxy)-8-(phenylamino)octane 7.0 Gm of 1-chloro-8-(1-naphthyloxy)octane was refluxed for 1 hour in 100 ml of aniline. The excess aniline was then removed under vacuum and the residue was distributed between methylene chloride and dilute aqueous potassium hydroxide. The organic solution was dried and evaporated, and the residue was chromatographed on silica gel, eluting with methylene chloride, so as to produce the title compound as an oil.

B. The preparation of
1-(1-naphthyloxy)-8-(phenylcyanoamino)octane 4.5 g of 1-(1-naphthyloxy)-8-(phenylamino)octane and 1.4 g of cyanogen bromide were heated in 150 ml of benzene at 55° for 2 hours. The benzene was then evaporated from the solution, affording 1-(1-naphthyloxy)-8-(phenylcyanoamino)octane which was employed in Step B (below) without further purification.

C. The preparation of 1,3-diphenyl-1-[8-(1-naphthyloxy)octyl]guanidine 5.25 Grams of 1-(1-naphthyloxy)-8-(phenylcyanoamino)octane and 15 ml of aniline were heated at 170° for 45 min. The excess aniline was removed under vacuum and the residue was chromatographed on a silica gel column eluting with a mobile phase of methylene chloride: methanol:ammonium hydroxide, 50:30:0.3, affording the title compound, (mp 132°–134° as the paratoluene sulphonate).

Similarly, using the procedures of A, B and C above, but employing other 1-chloro-ω-(anyloxy)alkanes instead of 1-chloro-8-(1-naphthyloxy)octane, and other amines instead of aniline, other 1,1,3-trisubstituted guanidines can be prepared.

EXAMPLE IV

Conversion of a free base to a salt 1,2-Dicyclohexyl-3-[2-(2-naphthyloxy)ethyl]guanidine phosphate 10.0 g of 1,3-dicyclohexyl-3-[2-(2-naphthyloxy)ethyl]guanidine was dissolved in ethanol (100 ml) and 5.7 g 85% phosphoric acid in 100 ml ethanol was added to this solution. After 16 hours 1400 ml ether was added to the solution. The resulting precipitate was removed by filtration and dried under vacuum to afford the title compound (mp 132°–134°).

In a similar manner, all compounds of Formula 1 in free base form may be converted to the acid addition salts by treatment with the appropriate acid, for example, hydrochloric acid, hydrobromic acid, sulfuric acid, nitric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE V

Conversion of a salt to a free base 10.0 g of 1,2-diphenyl-3-[6-(7-chloro-4-quinolinyl)hexyl]guanidine hydrochloride is dissolved in 500 ml water. An excess of aqueous sodium hydroxide is then added to the solution. The solution is extracted with methylene chloride and the extract is dried and evaporated to afford 1,2-diphenyl-3-[6-(7-chloro-4-quinolinyl)hexyl]guanidine.

In a similar manner, other salts of compounds of Formula 1 can be converted into the free bases.

EXAMPLE VI

Direct Interchange of acid addition salts 1.0 g of 1,2-dicyclohexyl-3-[6-(2-naphthyloxy)hexyl]guanidine acetate is dissolved in 50 ml water and a solution of 0.39 g of p-toluenesulphonic acid in 10 ml water is then added. The water is then evaporated under vacuum to afford 1,2-dicyclohexyl-3-[6-(2-naphthyloxy)hexyl]guanidine p-toluenesulphonate.

In a similar manner interchanges between other acid addition salts of compounds of Formula I can be made by treating with an appropriate inorganic or organic acid.

EXAMPLE VII

Inhibition of Carrageenan-Induced Pleural Inflammation

Male albino rats, weighing between 220 and 280 g, are administered an appropriate dose of a compound of Formula 1 by oral gavage. After 1 hour 0.3 ml of a 1% viscavin #402 solution is injected intrapleurally. Additional doses of the test compound are administered 24 and 48 hours after the intrapleural injections. After 72 hours the rats are sacrificed and the pleural cavities are exposed. The exudates are harvested and the total volume is measured. An aliquot is removed, diluted, and the number of cells is determined using a Coulter counter Compounds of Formula 1 effect a reduction, compared to undosed control animals, of both the volume of the exudate and the number of cells therein.

EXAMPLE VIII

Inhibition of Croton-oil Induced Ear Edema in the Rat

Male 21-day old rats are anesthetized and a solution of the test compound in 0.05 ml of a mixture of 20% pyridine, 5% water, 74% diethyl ether and 1% croton oil is applied to the inside and to the outside of the left ear. After 6 hours the ears of the anesthetized rats are removed and pieces of uniform size are punched out with an 8 mm punch. The ear pieces are then weighed. Compounds of Formula 1 effect an inhibition of the increase in weight of the treated ear.

What is claimed is:

1. A compound having the formula

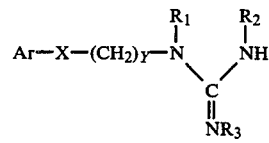

where
Ar is naphthyl, biphenyl, or quinolinyl;
X is oxygen or NH;
Y is 2 to 8;
$R_1$ is phenyl, substituted phenyl, hydrogen, or lower alkyl; and
$R_2$ and $R_3$ are each independently alkyl, cycloalkyl, phenyl, substituted phenyl, or thiazolyl;
or a pharmaceutically acceptable salt thereof.

2. The compound of claim 1 wherein
Ar is naphthyl or biphenyl;
X is oxygen; and
$R_2$ and $R_3$ are each independently alkyl, cycloalkyl, phenyl, substituted phenyl;
or a pharmaceutically acceptable salt thereof.

3. The compound of claim 2 wherein Ar is 1-naphthyl or 2-naphthyl, Y is 6 to 8, and X is 0.

4. The compound of claim 3 wherein $R_1$ is hydrogen.

5. The compound of claim 2 wherein $R_2$ and $R_3$ are phenyl or mono-substituted phenyl.

6. The compound of claim 4 wherein each of $R_2$ and $R_3$ is independently a substituted phenyl.

7. The compound of claim 6 wherein said substituted phenyl is an alkyl substituted phenyl.

8. The compound of claim 4 wherein $R_2$ and $R_3$ are each, independently, phenyl substituted with lower alkyl having one or two carbon atoms.

9. The compound of claim 8 wherein said alkyl substituted phenyl is a mono-substituted phenyl.

10. The compound of claim 9 wherein said phenyl is substituted in the 2 position.

11. The compound of claim 6 wherein said substituted phenyl is an alkoxy substituted phenyl.

12. The compound of claim 4 wherein $R_2$ and $R_3$ are each, independently, phenyl substituted with lower alkoxy having one or two carbon atoms.

13. The compound of claim 12 having only one lower alkoxy substituent on said phenyl.

14. The compound of claim 13 wherein said phenyl is substituted in the 2 position.

15. A compound having the formula:

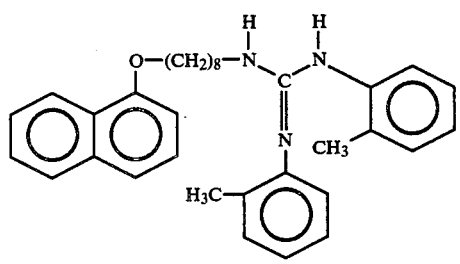

or a pharmaceutically acceptable salt thereof.

16. The hydrochloride salt of the compound of claim 15.

17. A compound having the formula

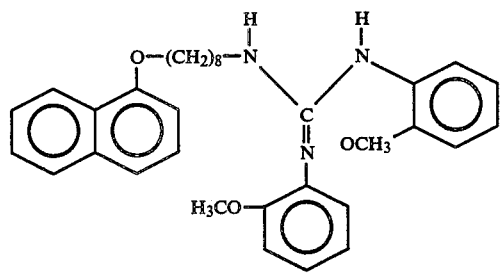

or a pharmaceutically acceptable salt thereof.

18. The hydrochloride salt of the compound of claim 17.

19. A pharmaceutical composition having anti-inflammatory activity or useful for the treatment of psoriasis which comprises an effective amount for the purpose intended of a compound of claim 1 and a pharmaceutically acceptable excipient.

20. A method for treating inflammation in mammals comprising administering a therapeutically effective amount of a compound having the formula

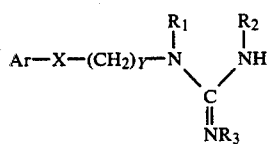

where
Ar is naphthyl, biphenyl, or quinolinyl;
X is oxygen or NH;
Y is 2 to 8;
$R_1$ is phenyl, substituted phenyl, hydrogen, or lower alkyl; and
$R_2$ and $R_3$ are each independently alkyl, cycloalkyl, phenyl, substituted phenyl, or thiazolyl;
or a pharmaceutically accpetable salt thereof.

21. A method for treating psoriasis in humans comprising topically administering a therapeutically effective amount of a compound having the formula

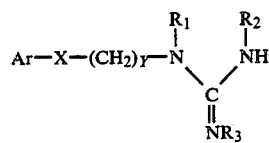

where
Ar is naphthyl, biphenyl, or quinolinyl;
X is oxygen or NH;
Y is 2 to 8;
$R_1$ is phenyl, substituted phenyl, hydrogen, or lower alkyl; and
$R_2$ and $R_3$ are each independently alkyl, cycloalkyl, phenyl, substituted phenyl, or thiazolyl;
or a pharmaceutically acceptable salt thereof.

* * * * *